(12) United States Patent
Futami et al.

(10) Patent No.: US 8,385,616 B2
(45) Date of Patent: Feb. 26, 2013

(54) SYSTEM FOR ASSISTING PREPARATION OF MEDICAL-IMAGE READING REPORTS

(75) Inventors: Hikaru Futami, Otawara (JP); Kenichi Niwa, Otawara (JP)

(73) Assignees: Kabushiki Kaisha Toshiba, Toyko (JP); Toshiba Medical Systems Corporation, Otawara-shi (JP)

( * ) Notice: Subject to any disclaimer, the term of this patent is extended or adjusted under 35 U.S.C. 154(b) by 409 days.

(21) Appl. No.: 12/422,405

(22) Filed: Apr. 13, 2009

(65) Prior Publication Data

US 2009/0262995 A1 Oct. 22, 2009

(30) Foreign Application Priority Data

Apr. 18, 2008 (JP) ................................. 2008-109322

(51) Int. Cl.
*G06K 9/00* (2006.01)
(52) U.S. Cl. ...................................................... 382/128
(58) Field of Classification Search .................. 382/128, 382/236; 600/407
See application file for complete search history.

(56) References Cited

U.S. PATENT DOCUMENTS

| | | | | |
|---|---|---|---|---|
| 6,482,156 B2 * | 11/2002 | Iliff | ............................... | 600/300 |
| 7,306,560 B2 * | 12/2007 | Iliff | ............................... | 600/300 |
| 7,386,153 B2 * | 6/2008 | Kim | ............................... | 382/128 |
| 2004/0073628 A1 * | 4/2004 | Usui | ............................... | 709/217 |
| 2005/0226405 A1 | 10/2005 | Fukatsu et al. | | |
| 2006/0058624 A1 * | 3/2006 | Kimura | ......................... | 600/407 |
| 2006/0184027 A1 * | 8/2006 | Watanabe et al. | ............ | 600/440 |
| 2006/0215897 A1 * | 9/2006 | Ando | ............................ | 382/132 |
| 2006/0271403 A1 | 11/2006 | Iwasa et al. | | |
| 2008/0051638 A1 * | 2/2008 | Iliff | ............................... | 600/300 |
| 2008/0051640 A1 * | 2/2008 | Iliff | ............................... | 600/300 |
| 2008/0064950 A1 * | 3/2008 | Ruohonen et al. | ........... | 600/411 |
| 2008/0253629 A1 * | 10/2008 | Kazuno et al. | ................ | 382/128 |
| 2008/0317309 A1 * | 12/2008 | Kazuno et al. | ................ | 382/128 |
| 2009/0116710 A1 * | 5/2009 | Futami et al. | ................. | 382/128 |
| 2009/0175519 A1 * | 7/2009 | Iizuka et al. | .................. | 382/128 |
| 2009/0306504 A1 * | 12/2009 | Arai et al. | ..................... | 600/443 |
| 2010/0067751 A1 * | 3/2010 | Aoki | ............................. | 382/118 |
| 2010/0195880 A1 * | 8/2010 | Ikeda | ........................... | 382/128 |

FOREIGN PATENT DOCUMENTS

JP 2005-301453 10/2005

* cited by examiner

*Primary Examiner* — Nathan Ha
(74) *Attorney, Agent, or Firm* — Oblon, Spivak, McClelland, Maier & Neustadt, L.L.P.

(57) ABSTRACT

A report-data collecting unit retrieves and collects a character string in accordance with the prescribed character-string retrieval condition and the character string of annotation data. An image data display unit displays the character string and a list showing a medical image referred to while the object is being photographed. When the user selects the character string by designating the medical image shown in the list, both the character string and the medical image are associated by an image-data acquisition/process unit and then pasted at a prescribed position in a medical-image reading report preparation screen. Further, the data representing the medical image thus pasted is archived in an image database.

9 Claims, 6 Drawing Sheets

FIG. 1

| Annotation character string | Display condition |
|---|---|
| Last time | CT |
| Pay attention! | If examined in the past |
| ... | ... |

| Hyperlinked character string | Display condition |
|---|---|
| In comparison with the last CT examination result | CT |
| In comparison with the last MR examination result, this time | If examined in the past |
| In comparison with the last CT examination result and the penultimate MR examination result | If not examined in the past |
| ... | ... |

| Hyperlinked character string | Display condition (number of times) |
|---|---|
| In comparison with the last CT examination result | 78 times |
| In comparison with the last MR examination result, this time | 21 times |
| In comparison with the last CT examination result and the penultimate MR examination result | 10 times |
| ... | ... |

F I G. 8

| To be hyperlinked? | Character string | Image |
|---|---|---|
| 1. ☐ | Last time | 🧠 |
| 2. ☑ | In comparison with this time | 🧠 |
| 3. ☐ | The tumor has grown larger | 🧠 |
| 4. ... | ... | ... |

F I G. 9

| Image link data | Image path |
|---|---|
| http://host/DicomViewer/<br>20060811/CT/1.2.XXXXXXX/<br>1.2.XXXXXX.dcm | ¥¥nas-b¥20060811¥CT¥<br>1.2.XXXXXXX¥1.2.<br>XXXXXX.dcm |
| http://host/DicomViewer/<br>20060821/MR/1.2.XXXXXXX/<br>1.2.XXXXXX.dcm<br><br>http://host/DicomViewer/<br>20060921/MR/1.2.XXXXXXX/<br>1.2.XXXXXX.dcm | ¥¥nas-b¥20060811¥CT¥<br>1.2.XXXXXXX¥1.2.<br>XXXXXX.dcm |
| http://host/DicomViewer/<br>20060801/MR/1.2.XXXXXXX/<br>1.2.XXXXXX.dcm<br><br>http://host/DicomViewer/<br>20060821/CT/1.2.XXXXXXX/<br>1.2.XXXXXX.dcm | Not examined in the past |
| ... | ... |

FIG. 10

SYSTEM FOR ASSISTING PREPARATION OF MEDICAL-IMAGE READING REPORTS

CROSS-REFERENCE TO RELATED APPLICATIONS

This application is based upon and claims the benefit of priority from prior Japanese Patent Application No. 2008-109322, filed Apr. 18, 2008, the entire contents of which are incorporated herein by reference.

BACKGROUND OF THE INVENTION

1. Field of the Invention

The present invention relates to a medical information system. More particularly, the invention relates to a system for assisting preparation of medical-image reading reports, for use in medical-image diagnosis workstations and image-diagnosis report preparation systems.

2. Description of the Related Art

To date, systems such as a medical-image diagnosis apparatus, a medical-image archiving apparatus, a medical-image diagnosis workstation, and an image-diagnosis report preparation system have been used. In such systems, reports are prepared as is known in the art. Each report consists of several medical images (key images) and text-data items (character strings), each associated with one medical image (see, for example, Jpn. Pat. Appln. KOKAI Publication No. 2005-301453).

Any user of the system can prepare and archive a report that consists of, as described above, text items and medical images associated with the respective images. However, it takes the user much time and labor to prepare a report, because he or she needs to input text-data items and associate each text-data item with the corresponding medical image.

More specifically, the user must i) input a text-data item even if he or she has input it before, ii) paste a key image again, if necessary, to the text-data item thus input, and iii) correct, if necessary, the text-data item to which the image has been pasted. Inputting the text-data item again lowers the efficiency of preparing the report. Pasting the key image again to the text-data item reduces the efficiency of reading images. Correcting the text-data items having a key image pasted to it requires complicated manual work.

BRIEF SUMMARY OF THE INVENTION

Accordingly, an object of the invention is to provide a system for assisting preparation of medical-image reading reports, which can collect text-data items to which key images should be pasted and images associated with these text-data items, can manage the text-data items and the images, thus collected, and can easily acquire a key-image/text-data candidate containing key-image data, whenever necessary.

A system for assisting preparation of medical-image reading reports, according to this invention, comprises: a medical-image storage unit archiving medical-image data; a medical-image reading report storage unit archiving a medical-image reading report; a collection unit configured to collect a character string of annotation data contained in the medical-image data or a character string associated with the medical image in the medical-image reading report, or both, from the medical-image storage unit or the medical-image reading report storage unit, or from both; a display unit configured to display the medical-image reading table or a reference image, or both, on a display screen; a display control unit configured to cause the display unit to display, at the same time, the medical image referred to while photographing an object and a list showing the character string; a selection unit configured to restrict the selection of the character string collected; an association unit configured to cause the selection unit to select a desired character string from the list, thereby associating the character string selected with the medical image; an input unit configured to insert the character string and the medical image associated to each other by the association unit, at a prescribed position on a report preparation screen, thereby preparing the medical-image reading report; and a data archiving unit configured to archive the image data representing the medical image associated with the character string inserted.

Another system for assisting preparation of medical-image reading reports, according to this invention, comprises: a medical-image storage unit archiving medical-image data; a medical-image reading report storage unit archiving a medical-image reading report; a collection unit configured to collect, under a specific condition, a character string of annotation data contained in the medical-image data or a character string associated with the medical image in the medical-image reading report, or both, from the medical-image storage unit or the medical-image reading report storage unit, or from both; a display unit configured to display an medical image of an object, a medical-image reading report about bout the medical image, and the character string collected by the collection unit; a selection unit configured to select a desired character train from the character train displayed by the display unit; and an edition unit configured to input the character string selected, to the medical-image reading report displayed by the display unit and to associate the medical-image reading report with the character string input.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described with reference to the accompanying drawings.

Figure 1:
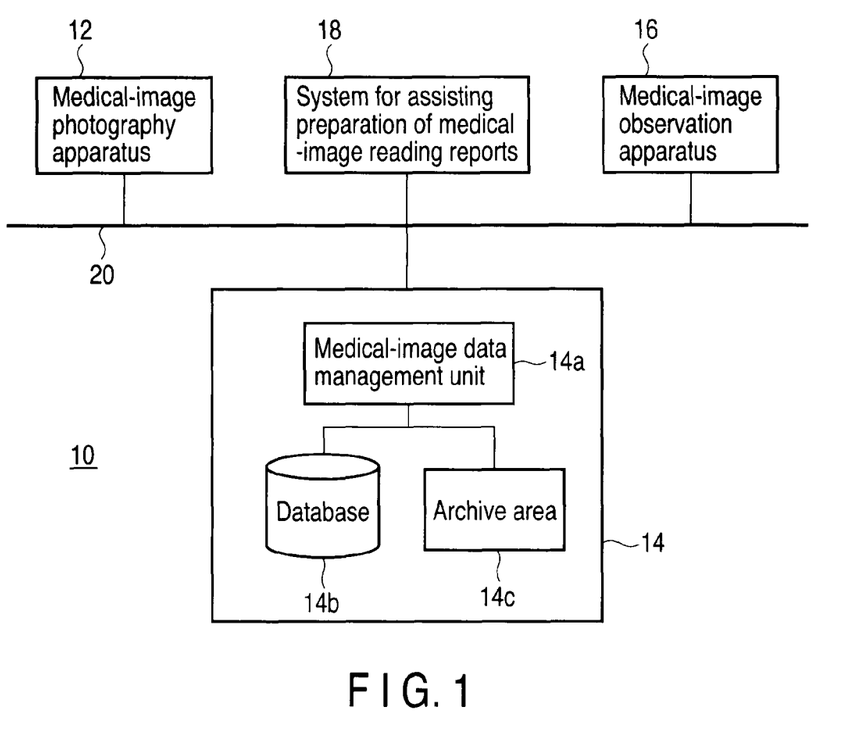
FIG. 1 is a block diagram showing the basic configuration of a medical data system according to an embodiment of this invention.

FIG. 1 is a block diagram showing the basic configuration of a medical data system 10 according to the present invention.

As shown in FIG. 1, the medical data system 10 comprises a medical-image photography apparatus 12, a medical-image storage apparatus 14, a medical-image observation apparatus 16, and a system 18 for assisting in preparation of a medical report. These apparatuses are connected by a communication line (LAN) 20 to communicate with each other. The medical-image photography apparatus 12 photographs, for example, the interior of a subject and generates image data (medical-image data). The image data generated will be used later in preparation of a medical-image reading report. The medical-image photography apparatus 12 is, for example, an ultrasonic diagnosis apparatus, an endoscope apparatus, an endoscope apparatus, an X-ray diagnosis apparatus, a CT apparatus, or an MRI apparatus. The image photographed is converted to digital image data of the DICOM format and transmitted to the medical-image storage apparatus 14.

The medical-image storage apparatus 14 has a medical-image data management unit 14a, a database 14b, and an archive area 14c. In the medical-image storage apparatus 14, the medical-image data management unit 14a associates the medical-image data items acquired in the medical-image photography apparatus 12, with one another. The medical-image data items are then compressed and stored in the database 14b and the archive area 14c. The medical-image storage apparatus 14 thus manages the medical-image data.

The medical-image observation apparatus 16 is configured to display images at a display such as a CRT. Observing and examining the images displayed, the user may diagnose the subject.

The system 18 for assisting in preparation of a medical report is designed to assist the user to prepare medical-image reading reports, on the basis of the medical images displayed by the medical-image observation apparatus 16.

Figure 2:
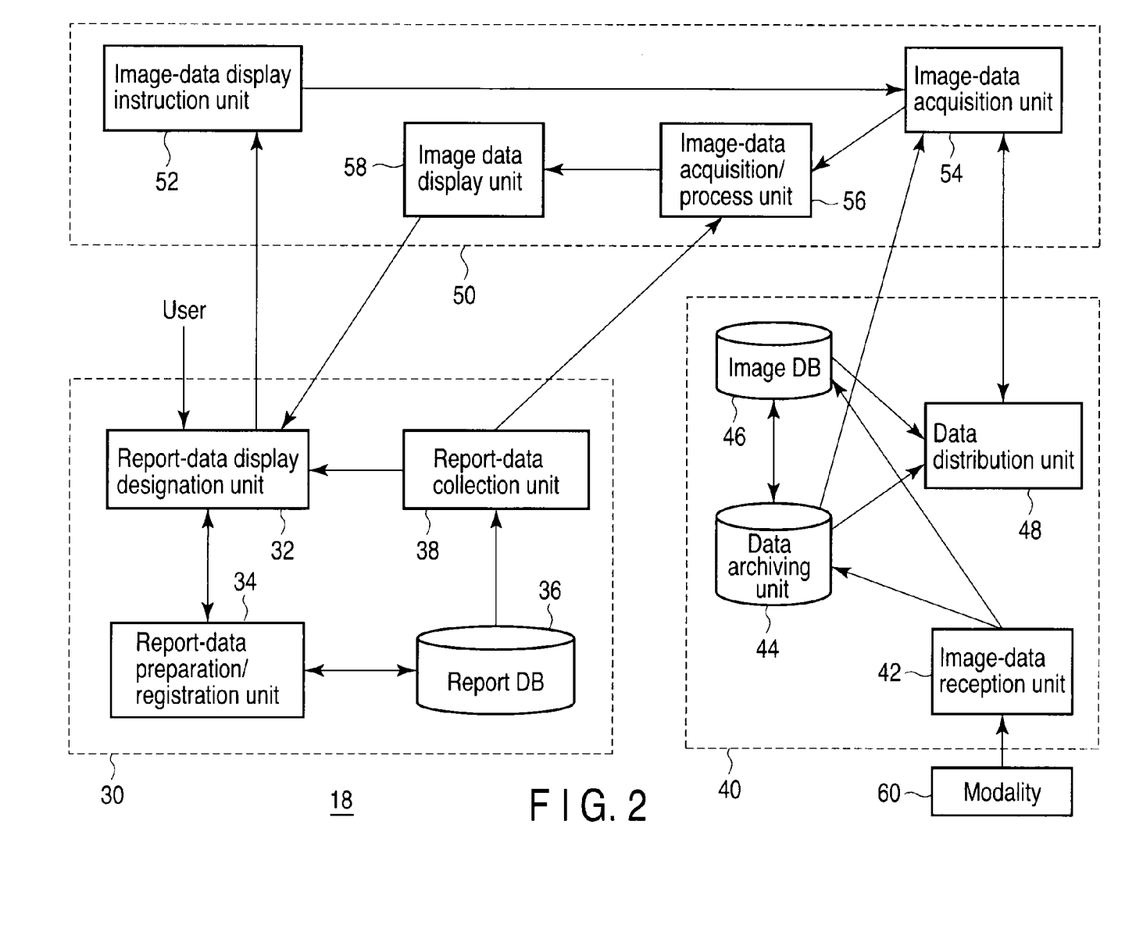
FIG. 2 is a block diagram showing the configuration of a system 18 for assisting preparation of medical-image reading reports, which is shown in FIG. 1.

FIG. 2 is a block diagram showing the configuration of the system 18 (FIG. 1) for assisting in preparation of a medical report.

The system 18 for assisting in preparation of a medical report is composed mainly of a report unit 30, a server unit 40, and a viewer unit 50.

The report unit 30 comprises a report-data display designation unit 32, a report-data preparation/registration unit 34, a report database (DB) 36, and a report-data collection unit 38.

The report-data display designation unit 32 displays various data items such as the report data requested for by the user, the report data being prepared in the report-data preparation/registration unit 34, and the data collected by the report-data collection unit 38. The report-data display designation unit 32 can output image-display instructions required in the process of displaying these various data items. If the user has input image-display instructions, the report-data display designation unit 32 may automatically output the image-display instructions selected from the linked data of the report. Further, the report-data display designation unit 32 can appropriately process a hyperlinked character string, if any, transmitted from an image-data display unit 58, which will be described later.

The report-data preparation/registration unit 34 manages the report data being processed to prepare a medical report. Any medical report prepared is transferred from report-data preparation/registration unit 34 to the report database 36. The report database 36 is a database configured to archive and manage report data items generated in the report-data preparation/registration unit 34. The report-data collection unit 38 is designed to collect and distribute any past report data items that are required, and to collect character/image-linked data items (representing the relation between character strings and images). The report-data collection unit 38 characterizes the present embodiment.

The server unit 40 comprises an image-data reception unit 42, a data archiving unit 44, an image database (DB) 46, and a data distribution unit 48 for distributing archived data.

The image-data reception unit 42 receives the image data coming from an external modality apparatus 60. The unit 42 then appropriately processes and archives the image data into the image database 46 and appropriately processes and archives the data accompanying the image data into the data archiving unit 44. The data archiving unit 44 receives the data accompanying the image data and associated with the image data, i.e., character strings (including character strings associated with various data items such as report-SINR data, key-image data, and pasted image). The data archiving unit 44 writes or archives the character strings in an appropriate archive area. If the archive area archiving the character strings is deleted or changed, the data archiving unit 44 communicates with the image database 46 and corrects the data representing the archive area. The data archiving unit 44 is equivalent to a plurality of HDDs, NASs or the like.

The image database 46 archives and manages data that requires the high-speed access of the data accompanying the image data received from the image-data reception unit 42. The archived-data distribution unit 48 collects the image requested for at any device, and distributes the image to the device.

The viewer unit 50 mentioned above has an image-data display instruction unit 52, an image-data acquisition unit 54, an image-data acquisition/process unit 56, and an image data display unit 58.

The image-data display instruction unit 52 instructs the image-data acquisition unit 54 to collect image data in accordance with the instruction given by the report-data display designation unit 32. In response to the instruction coming from the image-data display instruction unit 52, the image-data acquisition unit 54 collects necessary image data items and supplies the image data items to the image-data acquisition/process unit 56. The image-data acquisition unit 54 further acquires the annotation data accompanying the image, thus collecting the character string and the image constituting the annotation data (also collecting the data representing the relation between the character string and the image).

The image-data acquisition/process unit 56 receives data items from the image-data acquisition unit 54 and arranges these data items in order. The data items orderly arranged are sent from the image-data acquisition/process unit 56 to the image data display unit 58. The image-data acquisition/process unit 56 causes the image data display unit 58 to display only a group of images extracted and related to the character string so that these images may be corrected. Thus, an image related to any one of these images displayed can be added, corrected or deleted. Further, the image-data acquisition/process unit 56 demands for any list processed, sending the data required for generating the character string that should be pasted to a medical-image reading report and for combining the character string with the image associated with the character string, to the image data display unit 58.

The image data display unit 58 displays the image data and the list sent from the image-data acquisition/process unit 56, in accordance with a display instruction. Further, the image data display unit 58 supplies the report unit 30 with the data that should be transferred, as a hyperlinked character string, to the report unit 30.

How the medical data system 10 constituted as described above collects character strings will be explained with reference to the flowchart of FIG. 3.

To enable the user to prepare a medical-image reading report, the image data display unit 58 provided in the viewer unit 50 of the system 18 displays a report preparation screen and a reference medial image. The user operates, in most cases, a keyboard and/or a pointing device (e.g., mouse) to input text items that should be written in any medical-image reading report. Alternatively, the user may select and designate any one of data items registered beforehand, thereby to input the data item selected and designated.

Figure 4:
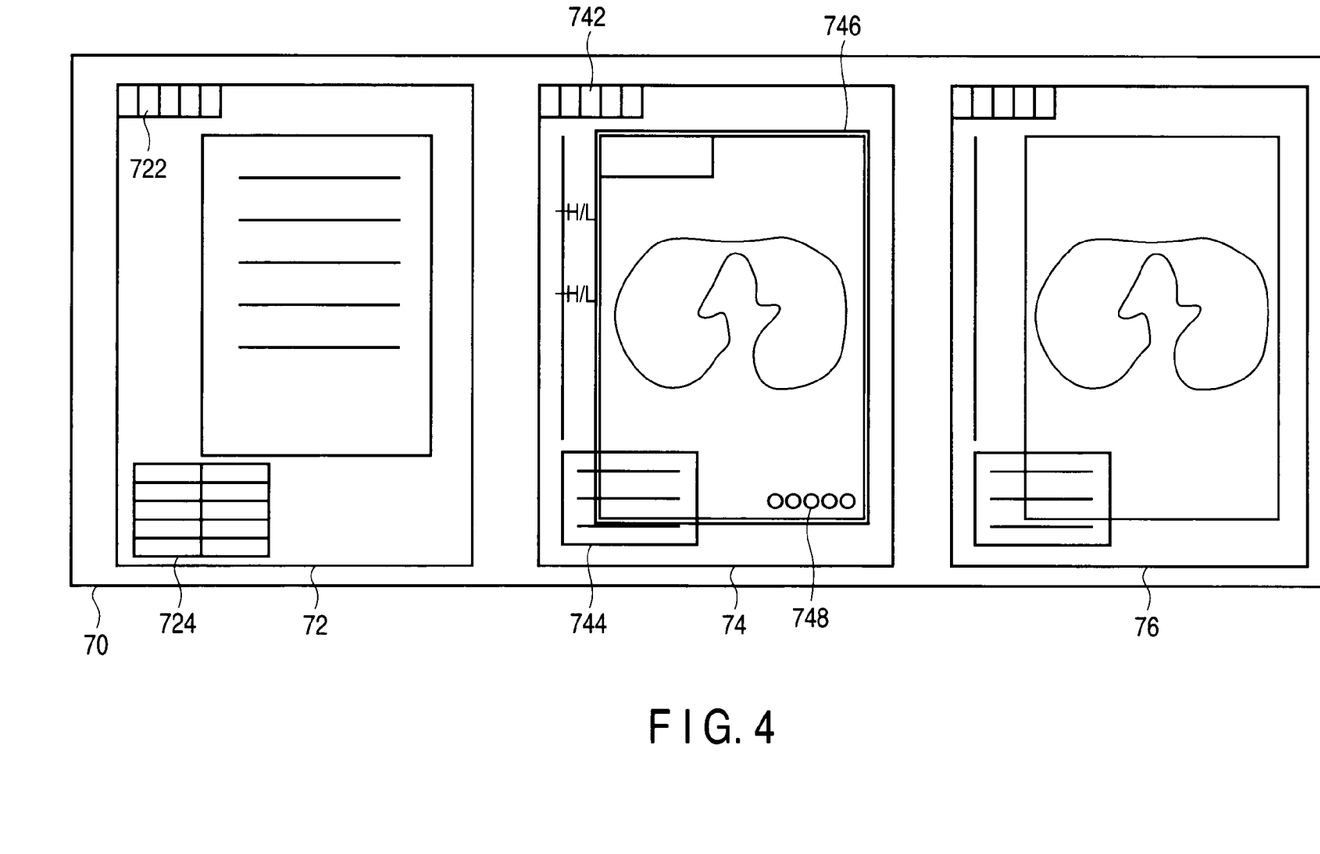
FIG. 4 is a diagram showing some images that a viewer 70 may display.

The image data display unit 58 constitutes a viewer 70, which has a screen 72. The screen 72 shows such a medical-image reading report as shown in FIG. 4. Character strings, i.e., comments on medical images, which the user has input, are arranged in the dedicated columns provided on the medical-image reading report. The character-string data items, e.g., hyperlinked data items or annotation data items are then collected. The report-data display designation unit 32 links the data items collected to a specific character string (Step S1). For example, the user moves the cursor to the character string displayed on the report preparation screen 72, designating the character string as one to be linked. Then, the user moves the cursor to one of the selection buttons 722 displayed on the screen 72, thus selecting a desired mode, for example the mode of collecting the character string designated.

At this point, whether the data about the character string collected exists is determined (Step S2). If the data exists, the character string is displayed in the lower part of the screen 72, as a list 724 of an appropriate form (see FIG. 9) (Step S3). The data of the reports made in the past are collected and distributed by the report-data collection unit 38. The report-data collection unit 38 also collects the character-string data (later described) and the image data, which should be linked to each other (to record the relation between them).

The report-data collection unit 38 manages the character strings of the annotation data items for the medical images of the same subject, which were photographed in the past, and the character strings associated with the annotation data items for a plurality of medical images examined in the past. Further, if the modality, the examined part of the subject, and the site identical to a key image acquired in the past are known from the specific related data (DICOM-accompanying data, etc.) under particular conditions, the character string concerned is collected and managed on the basis of the photographing site.

The report-data display designation unit 32 displays the report data requested by the user, the report data being prepared and the character-string data collected by the report-data collection unit 38.

Thereafter, in Step S4, the annotation character string selected, or hyperlinked character string selected, and, if necessary, the associated image are transmitted, as a data set, to the report-data display designation unit 32. The character string and the image, thus hyperlinked to each other in Step S4, are pasted to a prescribed position on the report preparation screen. This position is one of various choices including the user has preset, the end of a written comment and the end of the line pointed by the cursor.

At the time of photographing an object, acquiring an image, a mark may be put to the image associated with the above-mentioned character string, indicating the content of the image. For example, color, frame 746, a character string 748, or the like may be displayed in the image associated with the character string collected and referred to on a screen 74 shown in FIG. 4. Thus, any hyperlinked image may be distinguished from images not hyperlinked.

If no data about the character string collected exists (if No in Step S2), nothing is displayed in the screen 72 (Step S5).

The sequence is thus terminated.

The report-data preparation/registration unit 34 manages the report data being prepared, which the report-data display designation unit 32 displays. The report data completely prepared is sent to the report database 36 and managed in the report database 36.

How the character string associated with the medical image is displayed will be explained.

Figure 5:
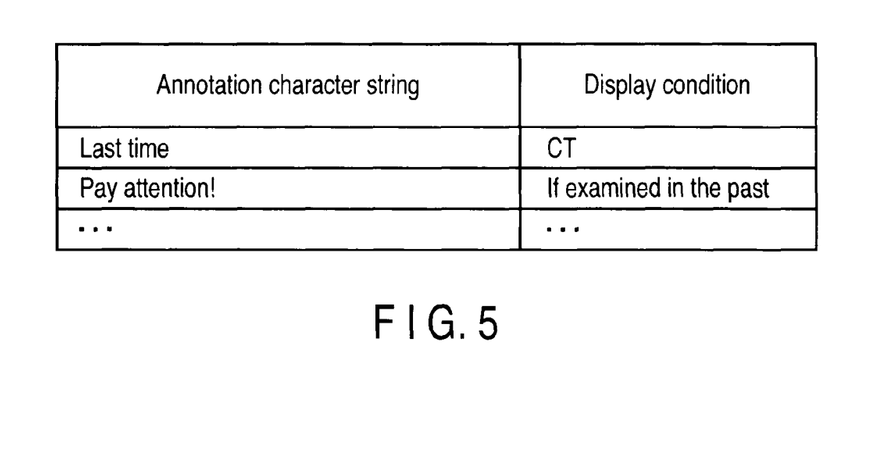
FIG. 5 is a table showing examples of annotation character-string data items collected.

FIG. 5 shows examples of annotation character-string data items that have been collected. Annotation character strings, such as "Previous time" and "Pay attention!," may be displayed. The annotation character strings are associated with conditions of "CT" and "If examined in the past," respectively.

Figure 6:
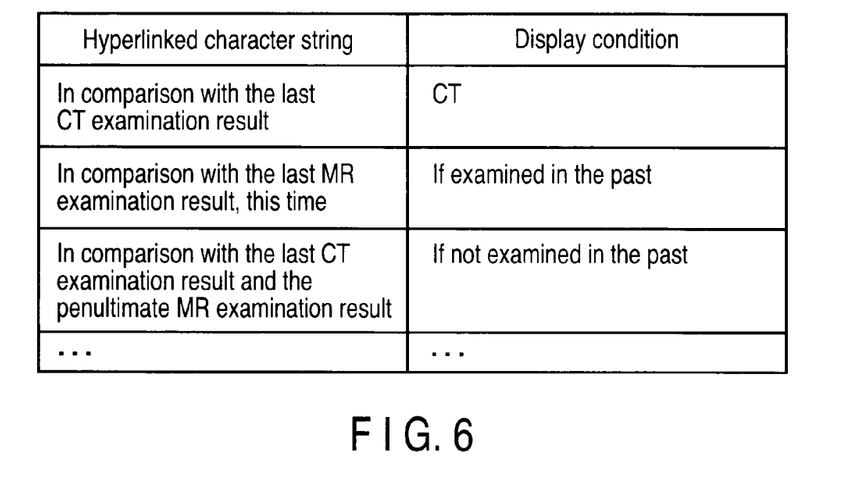
FIG. 6 is a table showing examples of hyperlinked character-string data items collected.

Similarly, FIG. 6 shows examples of hyperlinked character-string data items collected. These data items represent character strings "In comparison with the last CT examination result," "In comparison with the last MR examination result," "This time, in comparison with the last CT examination result and the penultimate MR examination result," and so on. These character strings are associated with the display conditions of "CT," "If examined in the past," and "If not examined in the past," respectively.

The report-data display designation unit 32 generates a hyperlinked character string, i.e., the collected character string linked to the image being observed at the time of photographing the object. A different character string may be associated with the image being currently displayed. This is because the character string that should be linked with the image being displayed may differ, depending on the attribute of the image being displayed at present. For example, any character string pertaining to an MR image is not displayed because it need not be displayed in the process of pasting a character string to a CT image. The condition for displaying hyperlinked character-string data thus changes. The character-string data may otherwise be collected in accordance with the condition for displaying it.

Figure 7:
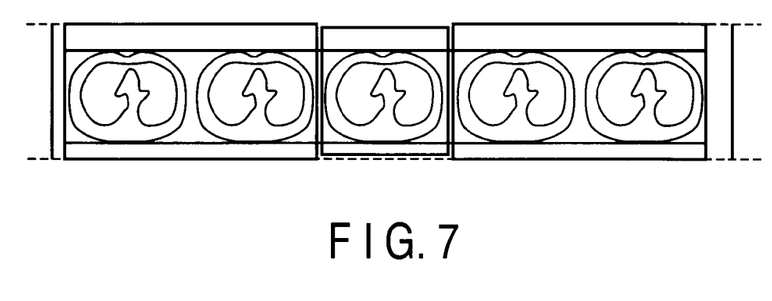
FIG. 7 is a diagram showing exemplary images for use in confirming images associated with hyperlinked character strings.

FIG. 7 shows exemplary images for use in confirming images that are associated with hyperlinked character strings. The exemplary images are associated with such hyperlinked character strings as shown in FIG. 5. These images are displayed, each in association with a hyperlinked character string. Note that two images may correspond to one hyperlinked character string. Moreover, an image can be added, corrected or deleted if it is related to the group of images being displayed.

Figure 8:
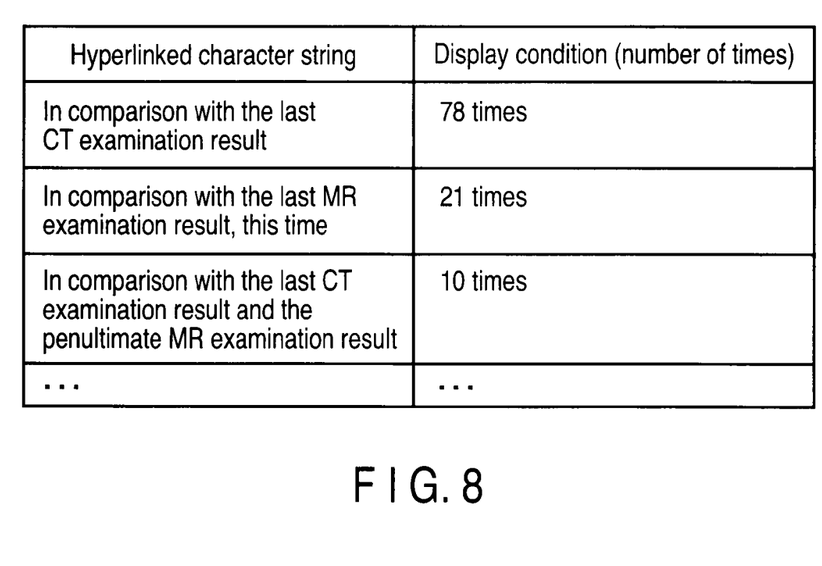
FIG. 8 is a table showing the number of times the hyperlinked character strings collected are used, each of which is displayed as a display condition.

FIG. 8 shows the number of times the hyperlinked character strings collected are used, each of which is displayed as a display condition. In this instance, the hyperlinked character strings available are: "In comparison with the result of the last CT examination result," "In comparison with the last MR examination result, "In comparison with the last CT examination result and the penultimate MR examination result," and the like. Also, the numbers of times these character strings were used in the past are displayed, which are "78 times," "21 times" and "10 times," respectively. The numbers of use times are displayed in the descending order.

Figure 3:
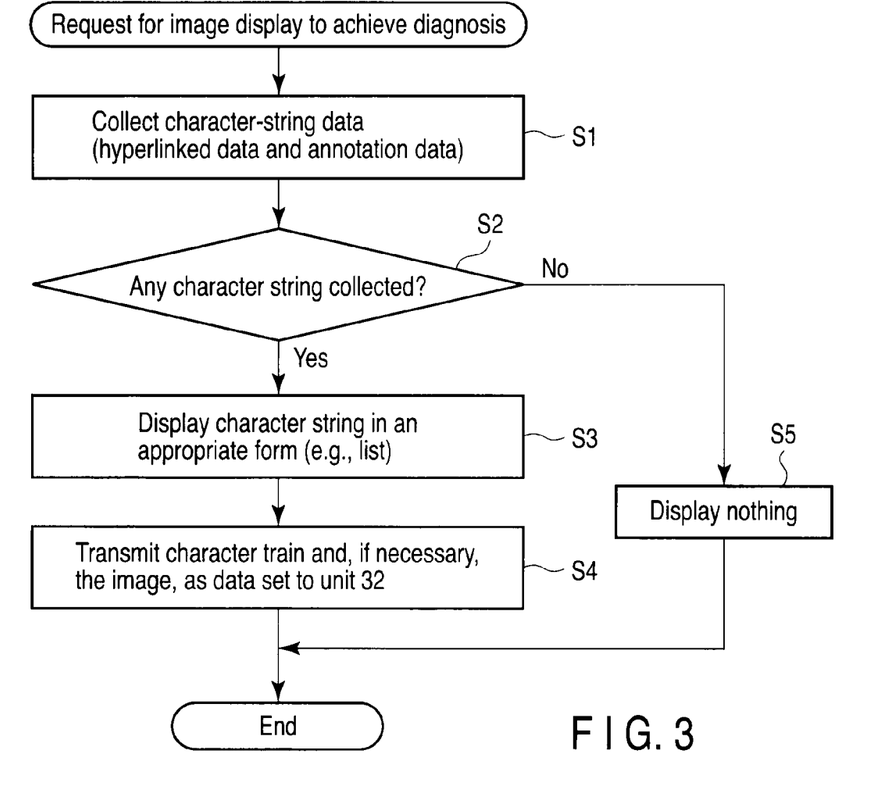
FIG. 3 is a flowchart explaining how the medical data system operates to collect character strings.
Figure 9:
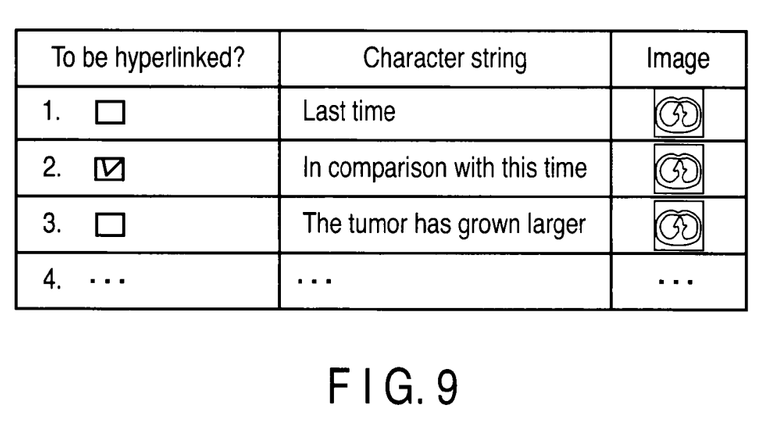
FIG. 9 shows an example of a character-string list displayed.

FIG. 9 shows an example of a character-string list displayed in Step S3 of the flowchart shown in FIG. 3. Items 1, 2, 3, 4, . . . are associated, each with a character string and an image. These data items are displayed in the descending order of the number of uses.

The user may operate the mouse or the like, attaching a check mark to the data item to hyperlink. Then, the desirable hyperlinked character string and the image, if any, associated with the hyperlinked character string are selected. In the case of the list shown in FIG. 9, the character string of item 2 is selected.

As pointed out above, a plurality of images, not one image, may correspond to one hyperlinked character string. Assume that there is a hyperlinked character string of, for example, "In comparison with this time with the past." Then, the list shows two images, one acquired at present, and the other acquired in the past. The two images will be hyperlinked to the character string selected if the character string is selected. In other words, a plurality of images may be hyperlinked to any character string that has been selected. Alternatively, if a specific image is hyperlinked to a character string, another specific image may be hyperlinked to the same character string, too. If a specific image is displayed on, for example, the screen 76, it may be hyperlinked, always to an image acquired in the past.

Figure 10:
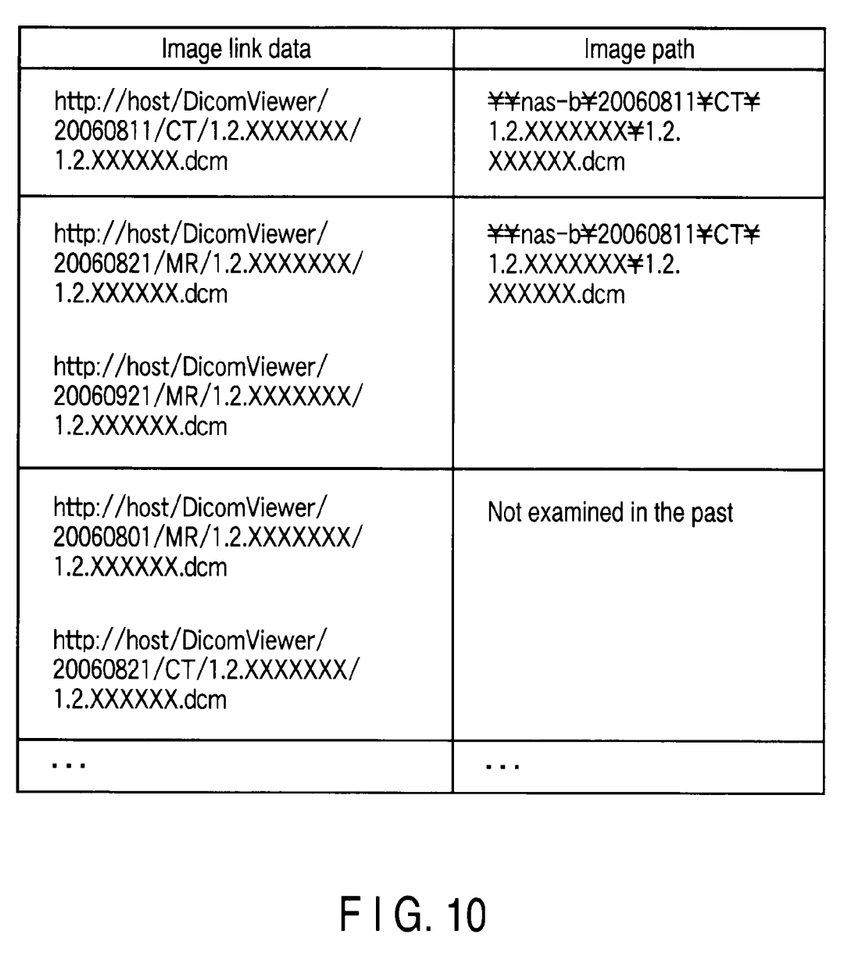
FIG. 10 is table showing exemplary image data items that are contained in the respective hyperlinked character strings.

FIG. 10 is table showing exemplary image data items that are contained in the respective hyperlinked character strings. As shown in FIG. 10, image paths are associated with respective image link data items, respectively.

In the process of preparing a report, for example, the user is looking at the image just acquired and displayed on the screen 74, while writing characters in the medical-image reading report. To hyperlink the desired image to the character string being written, the user operates the mouse or the like, clicking the selection button 742 displayed on the screen 74 and thereby selecting the desired mode. Then, the list 744 of FIG. 9, which contains the character-string data, is displayed in the lower part of the screen 72.

If the character-string data should be compared with character-string data acquired in the past, the image now displayed on the screen 74 and the image acquired in the past and displayed on the screen 76 will be hyperlinked together in the medical-image reading report.

Some images preceding an image hyperlinked to a certain character string and some other images following this image may be preset in order to recognize the hyperlinked image in the process of preparing the report, so that the preceding images and the following images may be displayed. Alternatively, only images that can be preset as those that can be hyperlinked to a certain character string may be read. In either case, the data about these images are collected, by adding annotations or marks to the images, by clicking the images or by double-clicking the images, and are then used as candidates that may be hyperlinked to the character string. The candidate images to hyperlink to the character string may be displayed in a scroll bar as illustrated in FIG. 4. Further, data pasted and edited may be fed back and input, in real time, as a choice in the list.

Since character strings prepared beforehand are thus associated with medical images, the character strings existing for use in reports can be utilized. That is, these character strings can be associated with the medical images, only if edited. This helps to increase the efficiency in preparing medical-image reading reports.

In the embodiment described above, the server unit comprises a data archiving unit and an image database and a data distribution unit, each used as data storage means for archiving medical-image data and medical-image reading reports. Nonetheless, this invention is not limited to this configuration. The medical-image data and the medical-image reading reports may be archived anywhere.

The present invention has been described with reference to an embodiment. The invention is not limited to the embodiment, nevertheless. Various changes and modifications can, of course, be made without departing from the scope and spirit of the invention.

Moreover, the embodiment described above pertains to various inventions. The components of the embodiment described above may be combined, if necessary, in appropriate ways, thereby to make different inventions. For example, some of the component of the embodiment may not be used or the components of the embodiment may be combined to solve the problems stated in the "Description of the Related Art." The advantages described in "BRIEF SUMMARY OF THE INVENTION" may be attained even if some components are omitted, thereby making an invention, too.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A system for assisting preparation of medical-image reading reports, comprising:
    a medical-image storage unit archiving medical-image data;
    a medical-image reading report storage unit archiving a medical-image reading report;
    a collection unit configured to collect a character string of annotation data contained in the medical-image data or a character string associated with the medical image in the medical-image reading report, or both, from the medical-image storage unit or the medical-image reading report storage unit, or from both;
    a display unit configured to display the medical-image reading report or a reference image, or both, on a display screen;
    a display control unit configured to cause the display unit to display, at the same time, the medical image referred to while diagnostic reading and a list showing the character string;
    a selection unit configured to restrict the selection of the character string collected;
    an association unit configured to cause the selection unit to select a desired character string from the list, thereby associating the character string selected with the medical image;
    an input unit configured to insert the character string and the medical image associated to each other by the association unit, at a prescribed position on a report preparation screen, thereby preparing the medical-image reading report; and
    a data archiving unit configured to archive the image data representing the medical image associated with the character string inserted.

2. The system according to claim 1, wherein the collection unit retrieves and collects a character string associated with a specific condition, in accordance with specific related data.

3. The system according to claim 1, wherein the display control unit changes the character string shown in the list, in accordance with an attribute of the reference image being displayed, in order to associate the reference image and the character string with each other, both displayed by the display unit.

4. The system according to claim 1, wherein the display control unit causes the display unit to display, in the list, only the image associated with the character string.

5. The system according to claim 1, wherein while the display unit is displaying the medical image associated with the character string collected, the display control unit causes the display unit to display the character train in the medical image.

6. A system for assisting preparation of medical-image reading reports, comprising:
   a medical-image storage unit archiving medical-image data;
   a medical-image reading report storage unit archiving a medical-image reading report;
   a collection unit configured to collect, under a specific condition, a character string of annotation data contained in the medical-image data or a character string associated with the medical image in the medical-image reading report, or both, from the medical-image storage unit or the medical-image reading report storage unit, or from both;
   a display unit configured to display a medical image of an object, a medical-image reading report about the medical image, and the character string collected by the collection unit;
   a selection unit configured to select a desired character string from the character string displayed by the display unit; and
   an edition unit configured to input the character string selected, to the medical-image reading report displayed by the display unit and to associate the medical-image reading report with the character string input.

7. The system according to claim 6, wherein a specific condition is determined by attribute data about the medical image currently being displayed.

8. A medical-image reading report generating apparatus, comprising:
   a collection unit configured to collect character strings of annotation data contained in medical-image data stored in a medical-image storage unit, or character strings associated with a medical image in a medical-image reading report, from the medical-image storage unit or a medical-image reading report storage unit; and
   a report-data display designation unit configured to associate one of the collected character strings desired by a user, with a reference medical image, and to attach the associated character string and the reference medical image to a preset portion of a medical-image reading report generating image.

9. A medical-image reading report generating apparatus, comprising:
   a collection unit configured to collect character strings of annotation data contained in a medical image, or character strings associated with the medical image in a medical-image reading report, from a medical-image storage unit or a medical-image reading report storage unit;
   a selection unit configured to select one of the character strings desired by a user; and
   a report-data display designation unit configured to input the selected character string to the medical-image reading report and associate the selected character string with a reference medical image on a display screen.

* * * * *

UNITED STATES PATENT AND TRADEMARK OFFICE
CERTIFICATE OF CORRECTION

PATENT NO. : 8,385,616 B2  
APPLICATION NO. : 12/422405  
DATED : February 26, 2013  
INVENTOR(S) : Hikaru Futami et al.

It is certified that error appears in the above-identified patent and that said Letters Patent is hereby corrected as shown below:

On the title page, Item (73), the first Assignee's information in incorrect, Item (73) should read:

--(73) Assignees: Kabushiki Kaisha Toshiba, Tokyo (JP)  
Toshiba Medical Systems Corporation, Otawara-shi (JP)--

Signed and Sealed this  
Eighteenth Day of June, 2013

Teresa Stanek Rea  
*Acting Director of the United States Patent and Trademark Office*